(12) United States Patent
Kawanabe et al.

(10) Patent No.: US 11,693,131 B2
(45) Date of Patent: Jul. 4, 2023

(54) RADIATION IMAGING APPARATUS AND RADIATION IMAGING SYSTEM

(71) Applicant: CANON KABUSHIKI KAISHA, Tokyo (JP)

(72) Inventors: Jun Kawanabe, Saitama (JP); Kentaro Fujiyoshi, Irvine, CA (US)

(73) Assignee: CANON KABUSHIKI KAISHA, Tokyo (JP)

(*) Notice: Subject to any disclaimer, the term of this patent is extended or adjusted under 35 U.S.C. 154(b) by 57 days.

(21) Appl. No.: 17/525,441

(22) Filed: Nov. 12, 2021

(65) Prior Publication Data
US 2022/0075085 A1 Mar. 10, 2022

Related U.S. Application Data

(63) Continuation of application No. PCT/JP2020/015692, filed on Apr. 7, 2020.

(30) Foreign Application Priority Data

May 29, 2019 (JP) ................................. 2019-100723

(51) Int. Cl.
*G01T 1/20* (2006.01)
*G01T 1/208* (2006.01)
(Continued)

(52) U.S. Cl.
CPC .......... *G01T 1/20181* (2020.05); *G01T 1/208* (2013.01); *H01L 27/14659* (2013.01); *H04N 25/40* (2023.01)

(58) Field of Classification Search
CPC ... G01T 1/20181; G01T 1/208; G01T 1/2008; G01T 1/20187; H01L 27/14659;
(Continued)

(56) References Cited

U.S. PATENT DOCUMENTS

| 8,878,972 B2 | 11/2014 | Wayama et al. |
| 9,270,903 B2 | 2/2016 | Wayama et al. |

(Continued)

FOREIGN PATENT DOCUMENTS

| JP | 2010-56396 A | 3/2010 |
| JP | 2011-22132 A | 2/2011 |

(Continued)

*Primary Examiner* — Kiho Kim
(74) *Attorney, Agent, or Firm* — Venable LLP

(57) ABSTRACT

A radiation imaging apparatus comprising a first scintillator, a second scintillator which receives radiation transmitted through the first scintillator, conversion elements and a controller is provided. The conversion elements include first conversion elements and second conversion elements with different sensitivities for detecting light emitted from at least one of the first scintillator or the second scintillator. During radiation irradiation, the controller obtains, from a signal output from one or more measuring element configured to measure a dose of incident radiation, a first signal corresponding to light converted from radiation by the second scintillator, and outputs, based on the first signal, a stop signal configured to stop the radiation irradiation, and after the radiation irradiation, the controller causes the first conversion elements and the second conversion elements to output signals configured to generate an energy subtraction image.

19 Claims, 10 Drawing Sheets

(51) Int. Cl.
*H01L 27/146* (2006.01)
*H04N 25/40* (2023.01)

(58) Field of Classification Search
CPC ......... H01L 27/14623; H01L 27/14663; H01L 31/08; H04N 25/40; H04N 5/32; A61B 6/00

See application file for complete search history.

(56) References Cited

U.S. PATENT DOCUMENTS

| | | | |
|---|---|---|---|
| 9,277,896 B2 | 3/2016 | Ofuji et al. | |
| 9,423,513 B2 | 8/2016 | Watanabe et al. | |
| 9,521,347 B2 | 12/2016 | Kawanabe et al. | |
| 9,625,585 B1 | 4/2017 | Yokoyama et al. | |
| 9,726,767 B2 | 4/2017 | Kawanabe et al. | |
| 9,661,240 B2 | 5/2017 | Fujiyoshi et al. | |
| 9,675,307 B2 | 6/2017 | Ofuji et al. | |
| 9,835,732 B2 | 12/2017 | Fujiyoshi et al. | |
| 9,838,638 B2 | 12/2017 | Furumoto et al. | |
| 9,948,871 B2 | 4/2018 | Wayama et al. | |
| 9,977,135 B2 | 5/2018 | Yokoyama et al. | |
| 10,068,943 B2 | 9/2018 | Fujiyoshi et al. | |
| 10,473,801 B2 | 11/2019 | Kawanabe et al. | |
| 10,537,295 B2 | 1/2020 | Watanabe et al. | |
| 10,634,800 B2 | 4/2020 | Yokoyama et al. | |
| 10,914,849 B2 | 2/2021 | Ofuji et al. | |
| 11,067,706 B2 | 7/2021 | Furumoto et al. | |
| 11,083,430 B2 | 8/2021 | Sato et al. | |
| 11,090,018 B2 | 8/2021 | Watanabe et al. | |
| 11,157,059 B2 | 10/2021 | Yokoyama et al. | |
| 2010/0054418 A1 | 3/2010 | Okada | |
| 2010/0061507 A1 | 3/2010 | Fujii | |
| 2013/0009069 A1* | 1/2013 | Okada | G01T 1/243 250/370.09 |
| 2013/0342514 A1 | 12/2013 | Yokoyama et al. | |
| 2014/0154833 A1 | 6/2014 | Wayama et al. | |
| 2018/0028141 A1* | 2/2018 | Kuwabara | A61B 6/56 |
| 2018/0031715 A1* | 2/2018 | Kuwabara | A61B 6/4266 |
| 2020/0124749 A1 | 4/2020 | Takenaka et al. | |
| 2020/0166659 A1 | 5/2020 | Fujiyoshi et al. | |
| 2020/0264319 A1 | 8/2020 | Takenaka | |
| 2020/0348424 A1 | 11/2020 | Watanabe et al. | |
| 2020/0371259 A1 | 11/2020 | Miura et al. | |
| 2022/0011452 A1 | 1/2022 | Ryu et al. | |

FOREIGN PATENT DOCUMENTS

| | | |
|---|---|---|
| JP | 2018-23769 A | 2/2018 |
| JP | 2018-186468 A | 11/2018 |
| WO | 2008/120293 A1 | 10/2008 |
| WO | 2019/093168 A1 | 5/2019 |

* cited by examiner 901  902

901  902

901 902

901 902

RADIATION IMAGING APPARATUS AND RADIATION IMAGING SYSTEM

CROSS-REFERENCE TO RELATED APPLICATIONS

This application is a Continuation of International Patent Application No. PCT/JP2020/015692, filed Apr. 7, 2020, which claims the benefit of Japanese Patent Application No. 2019-100723, filed May 29, 2019, both of which are hereby incorporated by reference herein in their entirety.

BACKGROUND OF THE INVENTION

Field of the Invention

The present invention relates to a radiation imaging apparatus and a radiation imaging system.

Background Art

As an imaging apparatus used in medical image diagnosis or nondestructive inspection, a radiation imaging apparatus that includes an imaging panel in which pixels each formed by combining a conversion element for converting radiation into a charge and a switch element such as a thin-film transistor (TFT) are arrayed is widely used. There is known a method that uses such a radiation imaging apparatus to obtain a plurality of radiation images by using radiation beams of different energy components to obtain, from a difference between the obtained radiation images, an energy subtraction image in which a specific portion of an object is isolated or emphasized. PTL 1 discloses that scintillators are arranged on both surfaces of a substrate, and a photodiode for detecting light emitted by a scintillator on one side and a photodiode for detecting light emitted by a scintillator on the other side are arranged. By using photodiodes that detect light beams emitted from different scintillators, two different energy component signals can be obtained by one radiation irradiation operation, thus allowing an energy subtraction image to be generated.

CITATION LIST

Patent Literature

PTL 1: Japanese Patent Laid-Open No. 2010-056396

Among the scintillators arranged on both surfaces of the substrate, a low energy radiation beam among incident radiation beams is converted into light by a scintillator on a radiation incident side and a high energy radiation beam is converted into light in a scintillator arranged on a side opposite to the radiation incident side. After being transmitted through the scintillator on the radiation incident side and the substrate, a high energy radiation beam is converted into light by a scintillator on the side opposite to the radiation incident side. Hence, the radiation dose will decrease. As a result, the signal value of a signal corresponding to the high energy radiation beam will decrease, and the image quality of the generated energy subtraction image may be degraded.

An object of the present invention is to provide a technique advantageous in suppressing image quality degradation of an energy subtraction image.

SUMMARY OF THE INVENTION

According to some embodiments, a radiation imaging apparatus that comprises a first scintillator, a second scintillator which receives radiation transmitted through the first scintillator, a plurality of conversion elements, and a controller, wherein the plurality of conversion elements include a plurality of first conversion elements and a plurality of second conversion elements with different sensitivities for detecting light emitted from at least one of the first scintillator or the second scintillator, and during radiation irradiation, the controller is configured to obtain, from a signal output from not less than one measuring element configured to measure a dose of incident radiation among the plurality of first conversion elements and the plurality of second conversion elements, a first signal corresponding to light converted from radiation by the second scintillator among the first scintillator and the second scintillator, and output, based on the first signal, a stop signal configured to stop the radiation irradiation to the radiation imaging apparatus, and after the radiation irradiation, the controller is configured to cause the plurality of first conversion elements and the plurality of second conversion elements to output signals configured to generate an energy subtraction image, is provided.

According to some other embodiments, a radiation imaging apparatus that comprises a first conversion element, a second conversion element, and a controller, wherein the first conversion element and the second conversion element have different sensitivities for detecting light, and the controller is configured to output, using a signal output from a measuring element configured to measure a dose of incident radiation, a stop signal configured to stop the radiation irradiation to the radiation imaging apparatus, and cause the first conversion element and the second conversion element to output signals configured to generate an energy subtraction image, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

DESCRIPTION OF THE EMBODIMENTS

Figure 1:
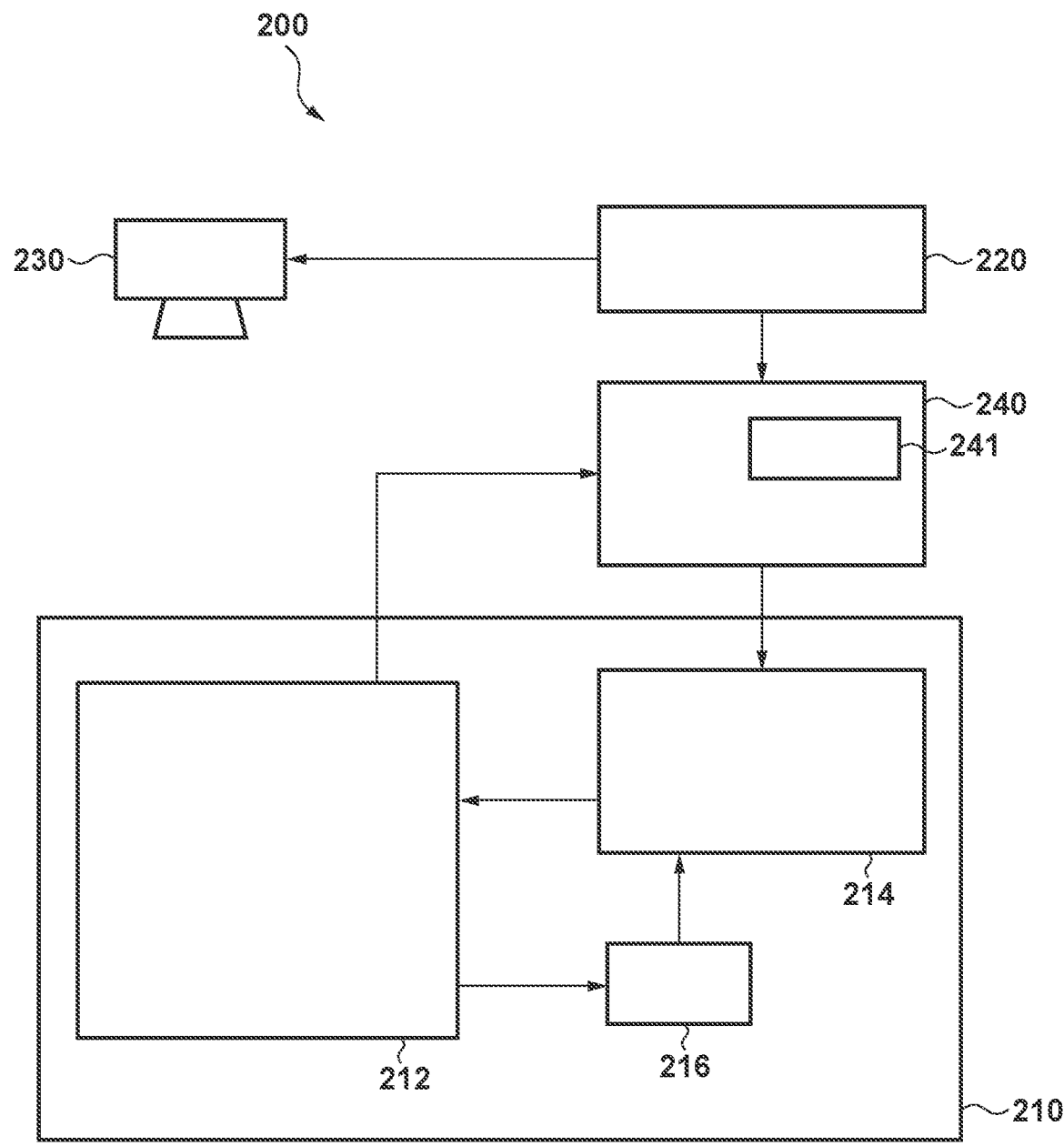
FIG. 1 is a block diagram showing an example of the arrangement of a radiation imaging system using a radiation imaging apparatus according to an embodiment of the present invention.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

Radiation according to the present invention can include not only α-rays, β-rays, and γ-rays that are beams generated by particles (including photons) emitted by radioactive decay but also beams having equal or more energy, for example, X-rays, particle rays, and cosmic rays.

An arrangement and an operation of a radiation imaging apparatus according to an embodiment will be described with reference to FIGS. 1 to 8. FIG. 1 is a block diagram showing an example of the arrangement of a radiation imaging system 200 using a radiation imaging apparatus 210 according to the embodiment of the present invention. The radiation imaging system 200 is formed to electrically capture an optical image which is converted from radiation and obtain an electrical signal (radiation image data) for generating a radiation image. The radiation imaging system 200 includes, for example, the radiation imaging apparatus 210, a radiation source 230, an irradiation controller 220, and a computer 240.

The radiation source 230 starts emitting radiation in accordance with an exposure instruction (radiation instruction) from the irradiation controller 220. The radiation emitted from the radiation source 230 passes through an object (not shown) and irradiates the radiation imaging apparatus 210. The radiation source 230 also stops emitting radiation in accordance with a stop instruction from the irradiation controller 220.

The radiation imaging apparatus 210 includes an imaging panel 212 and a controller 214 for controlling the imaging panel 212. The controller 214 generates, based on a signal obtained from the imaging panel 212, a stop signal for stopping the emission of radiation from the radiation source 230. The stop signal is supplied to the irradiation controller 220, and the irradiation controller 220 will transmit the stop instruction to the radiation source 230 in response to the stop signal. The controller 214 can be formed by, for example, a PLD (the abbreviation of a Programmable Logic Device) such as an FPGA (the abbreviation of a Field Programmable Gate Array), an ASIC (the abbreviation of an Application Specific Integrated Circuit), a general-purpose computer in which a program is installed, or a combination of all or some of these components.

The computer 240 controls the radiation imaging apparatus 210 and the irradiation controller 220. The computer 240 also includes a signal processor 241 that receives the radiation image data output from the radiation imaging apparatus 210 and processes the radiation image data. The signal processor 241 can generate a radiation image from the radiation image data.

The irradiation controller 220 includes, as an example, an exposure switch (not shown), transmits, when a user has set the exposure switch to ON, an exposure instruction to the radiation source 230, and transmits a start notification which indicates the start of radiation emission to the computer 240. Upon receiving the start notification, the computer 240 will notify, in response to the start notification, the controller 214 of the radiation imaging apparatus 210 of the start of radiation emission.

Figure 2:
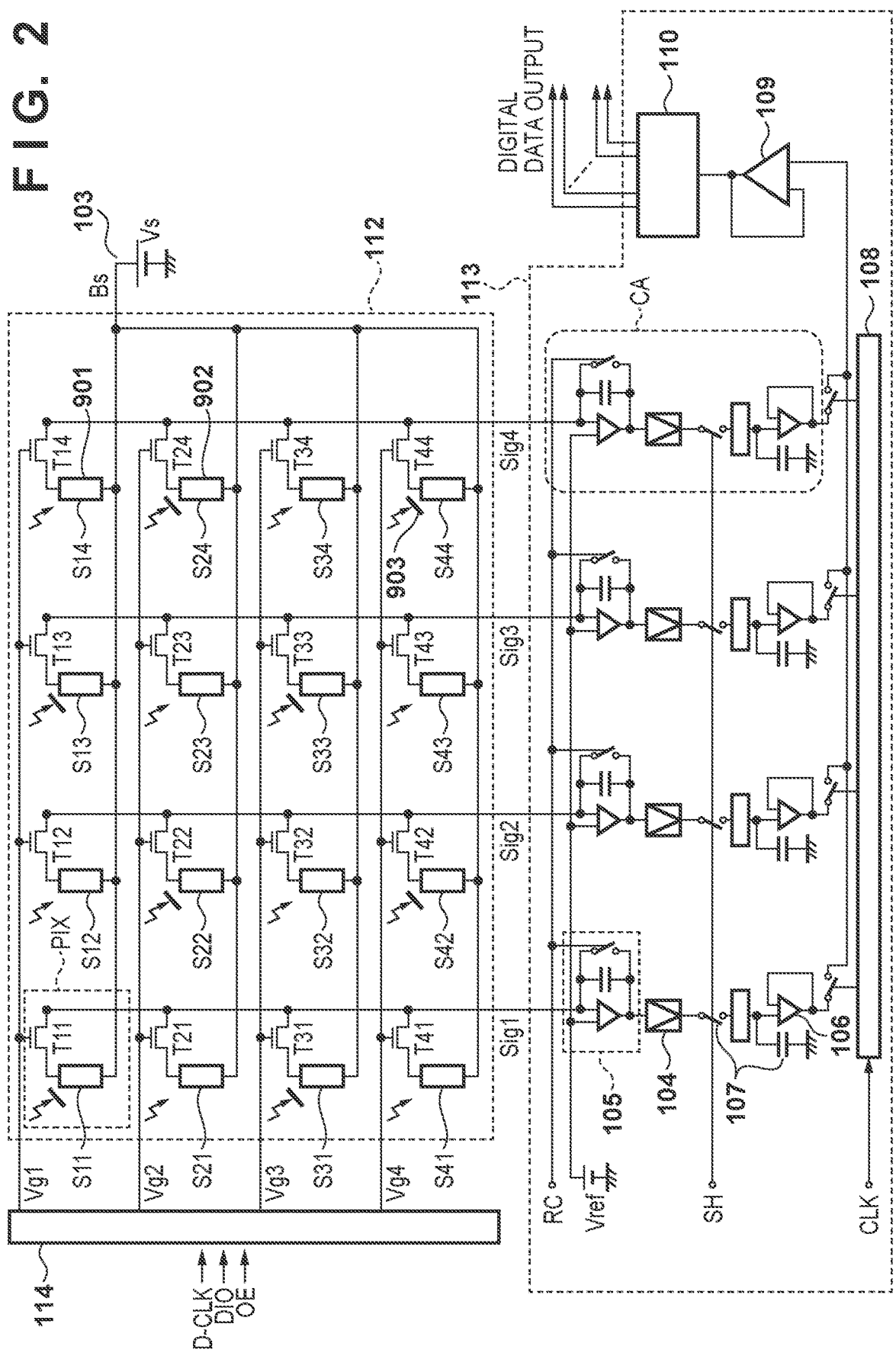
FIG. 2 is a block diagram showing an example of the arrangement of an imaging panel of the radiation imaging apparatus of FIG. 1.

FIG. 2 shows an example of the arrangement of the imaging panel 212. The imaging panel 212 includes a pixel array 112. The pixel array 112 includes a plurality of pixels PIX each including a conversion element S (photoelectric conversion element) arranged in a two-dimensional array and used for detecting radiation. The pixel array 112 also includes a plurality of column signal lines Sig1 to Sig4 arranged along a column direction (a vertical direction in FIG. 2) and used for outputting signals generated by the conversion elements S.

Furthermore, the imaging panel 212 includes a driving circuit (row selection circuit) 114 that drives the pixel array 112 and a readout circuit 113 that detects a signal which appears in each signal line Sig of the pixel array 112. Although the pixel array 112 is formed by 4 (rows)×4 (columns) of the pixels PIX for the sake of descriptive convenience in the arrangement shown in FIG. 2, many more pixels PIX can be arranged in practice. In an example, the imaging panel 212 can be 17 inches in dimension and include about 3,000 (rows)×3,000 (columns) of the pixels PIX.

Each pixel PIX includes the conversion element S for detecting radiation and a switch T which connects the conversion element S to the column signal line Sig (the signal line Sig corresponding to a conversion element S among the plurality of signal lines Sig). Each conversion element S outputs, to the corresponding column signal line, a signal corresponding to the amount of incident radiation. The conversion element S can be, for example, a MIS photodiode mainly made of an amorphous silicon and arranged on an insulating substrate such as a glass substrate or the like. Alternatively, the conversion element S may be a PIN photodiode. In this embodiment, the conversion element S can be formed as an indirect-type element that detects light after the radiation has been converted into light by a scintillator. In an indirect-type element, the scintillator can be shared by the plurality of the pixels PIX (the plurality of conversion elements S).

Each switch T can be formed by, for example, a transistor such as a thin film transistor (TFT) or the like that includes a control terminal (gate) and two main terminals (a source and a drain). Each conversion element S includes two main electrodes. One main electrode of the conversion element S is connected to one of the two main terminals of the corresponding switch T, and the other main electrode of the conversion element S is connected to a bias power supply 103 via a common bias line Bs. The bias power supply 103 supplies a bias voltage Vs. The control terminal of the switch T of each pixel PIX arranged in the first row is connected to a gate line Vg1 arranged along a row direction (a horizontal direction in FIG. 2). In a similar manner, the control terminal of a switch T of each pixel PIX arranged in each of the second row to the fourth row is connected to the corresponding one of gate lines Vg2 to Vg4. The driving circuit 114 supplies a gate signal to each of the gate lines Vg1 to Vg4.

In each pixel PIX arranged in the first row, a main terminal, of the switch T, which is on a side not connected to the conversion element S is connected to the column signal line Sig1 of the first column. In a similar manner, in each pixel PIX of arranged in each of the second column to the fourth column, the main terminal, of the switch T, which is on the side not connected to the conversion element S, is connected to the corresponding one of the column signal line Sig2 to the column signal line Sig4 of the second column to the fourth column.

The readout circuit 113 includes a plurality of column amplification units CA so that one column amplification unit CA will correspond to one column signal line Sig. Each column amplification unit CA can include an integrating amplifier 105, a variable amplifier 104, a sample-and-hold circuit 107, and a buffer circuit 106. The integrating amplifier 105 amplifies a signal that has appeared in the column signal line Sig. The integrating amplifier 105 can include an operational amplifier, an integrating capacitor parallelly connected to an inverting input terminal and an output terminal of the operational amplifier, and a reset switch. A reference potential Vref is supplied to the non-inverting input terminal of the operational amplifier. Setting the reset switch to ON will reset the integrating amplifier and reset the potential of the column signal line Sig to the reference potential Vref. The reset switch can be controlled by a reset pulse RC supplied from the controller 214.

A signal output from the integrating amplifier 105 is amplified by the variable amplifier 104 by a set amplification factor. The sample-and-hold circuit 107 samples and holds the signal output from the variable amplifier 104. The sample-and-hold circuit 107 can be formed by a sampling switch and a sampling capacitor. The buffer circuit 106 buffers (executes impedance transformation of) the signal output from the sample-and-hold circuit 107 and outputs the buffered signal. The sampling switch can be controlled by a sampling pulse supplied from the controller 214.

The readout circuit 113 also includes a multiplexer 108 that selects and outputs, in a predetermined order, each signal from the plurality of column amplification units CA arranged in correspondence with the respective column signal lines Sig. The multiplexer 108 includes, for example, a shift register. The shift register executes a shifting operation in accordance with a clock signal CLK supplied from the controller 214, and the shift register selects one signal from the plurality of column amplification units CA. The readout circuit 113 can further include a buffer 109 which buffers (executes impedance transformation of) the signal output from the multiplexer 108 and an A/D converter 110 which converts an analog signal as the signal output from the buffer 109 into a digital signal. The output, that is, the radiation image data from the A/D converter 110 is transferred to the computer 240.

In this embodiment, as will be described later, scintillators for converting radiation into visible light are arranged on both sides of a substrate, that is, on the side of an incident surface for allowing radiation to enter and on the side opposite to the incident surface, so as to cover the respective surfaces. In addition, the conversion elements S included in the respective pixels PIX include two kinds of conversion elements S. In the arrangement shown in FIG. 2, conversion elements S12, S14, S21, S23, S32, S34, S41, and S43 are arranged so as to receive light beams from the two scintillators. When these conversion elements which receive light from the two scintillators are to be specified among the conversion elements S, they will be referred to as conversion elements 901 hereinafter. In addition, in each of conversion elements S11, S13, S22, S24, S31, S33, S42, and S44, a light-shielding layer 903 is arranged between one scintillator and the conversion element S. As a result, the conversion elements S11, S13, S22, S24, S31, S33, S42, and S44 are arranged so that light from one scintillator will be shielded or reduced and light from the other scintillator will be received. When these conversion elements to which light from one scintillator is shielded or reduced are to be specified among the conversion elements S, they will be referred to as conversion elements 902 hereinafter. Each light-shielding layer 903 is a layer that shields the light emitted from the scintillator, and suffices to shield the light between the corresponding conversion element 902 and either the scintillator covering the side of the incident surface of the substrate or the scintillator covering the side of the back surface of the substrate. At this time, the light from one scintillator may not be completely shielded in the conversion element 902. It is sufficient as long as the light-shielding layer 903 is arranged between the conversion element 902 and one of the scintillator covering the side of the incident surface of the substrate and the scintillator covering the side of the back surface of the substrate so that the amount of light which can be received from the one scintillator will be less than the conversion element 901.

Assume here that the light-shielding layer 903 is arranged between each conversion element 902 and the scintillator arranged on the side of the incident surface of the substrate. A low energy component of the radiation that entered from the side of the incident surface of the substrate is absorbed and converted into visible light by the scintillator covering the side of the incident surface of the substrate, and enters each pixel PIX. Since the light-shielding layer 903 is arranged between each conversion element 902 and the scintillator arranged on the side of the incident surface of the substrate, light emitted from the scintillator on the side of the incident surface of the substrate does not enter each conversion element 902. Hence, the light converted from the low energy component of the radiation does not enter each conversion element 902. On the other hand, the light converted from the low energy component of the radiation will enter each conversion element 901 since the light-shielding layer 903 is not provided in each conversion element 901.

Also, a high energy component of the radiation which was not absorbed by the scintillator arranged on the side of the incident surface of the substrate is absorbed and converted into visible light by the scintillator covering the side of the back surface of the substrate. Since the conversion elements 901 and the conversion element 902 are not shielded from light from the side of the back surface of the substrate, the light converted from the high energy component of the radiation will enter both the conversion elements 901 and the conversion elements 902. As a result, the conversion elements S can use a simple element structure to efficiently receive the light beams emitted from the scintillators arranged on the incident surface and the back surface.

In this manner, a signal caused by a high energy component and a low energy component of the radiation can be obtained in each conversion element 901, and a signal caused by a high energy component of the radiation can be obtained in each conversion element 902. That is, different pieces of radiation energy information can be held by the pixels PIX arranged adjacent to each other. By holding pieces of information obtained from different energy components of the radiation in the adjacent pixel PIX in this manner, it will be possible to execute energy subtraction by using a method to be described later.

Figure 3A:
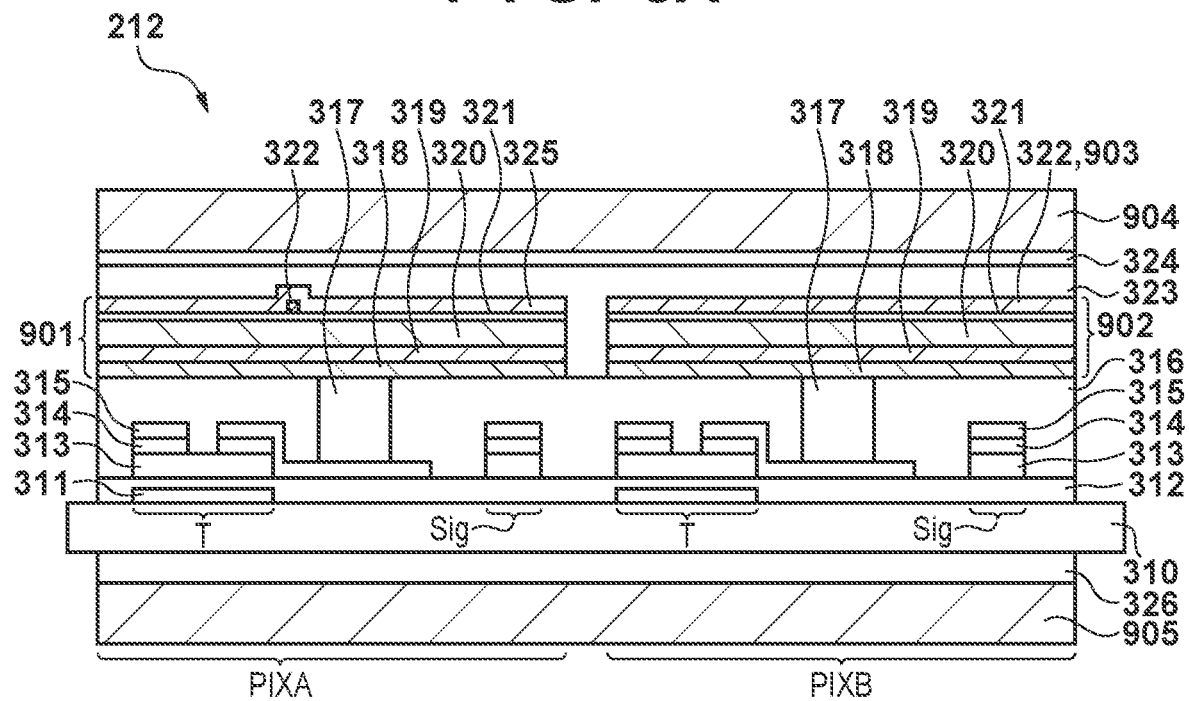
FIG. 3A is a view showing an example of the structure of a section of pixels of the radiation imaging apparatus of FIG. 1.
Figure 3B:
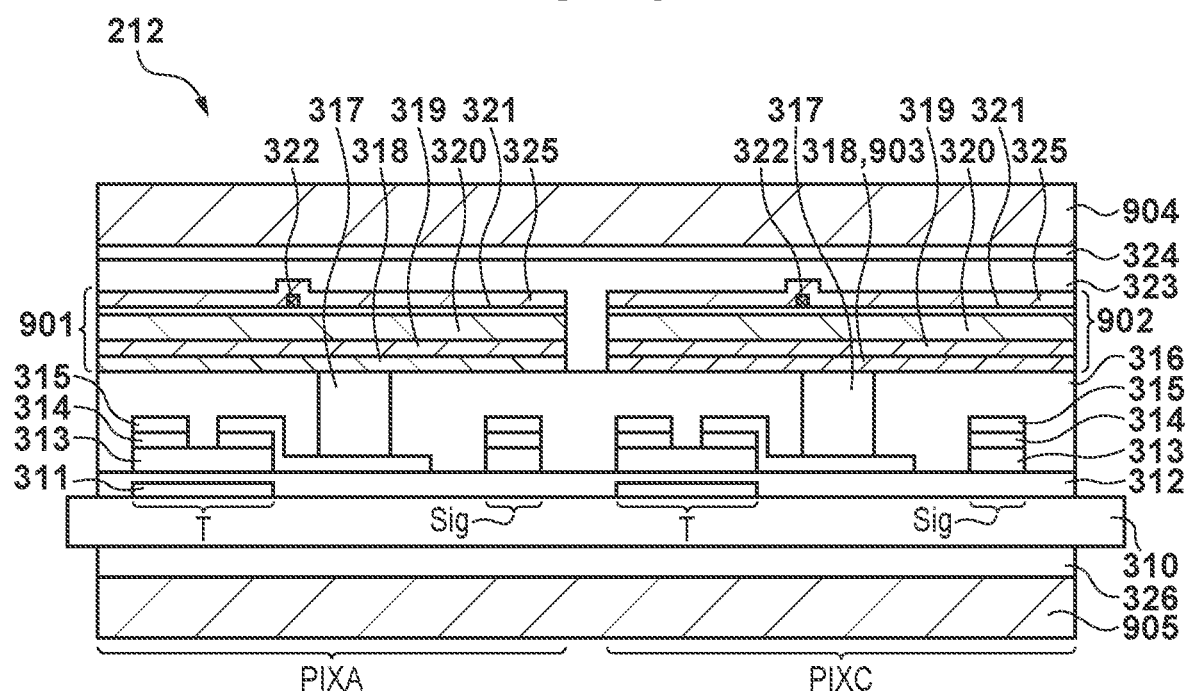
FIG. 3B is a view showing an example of the structure of the section of the pixels of the radiation imaging apparatus of FIG. 1.

FIGS. 3A and 3B schematically show an example of the sectional structure of a pixel PIXA holding the conversion element 901 and pixels PIXB and PIXC each holding the conversion element 902 which are arranged in the imaging panel 212. Although it will be described here that the radiation will enter from the upper side of FIGS. 3A and 3B, the radiation may enter from the lower side of FIGS. 3A and 3B. In either case, the scintillator arranged on the radiation incident side will emit light mainly caused by the low energy component of the radiation, and the scintillator arranged on the other side will emit light mainly caused by the high energy component of the radiation. In FIG. 3A, the conversion element 901 and the conversion element 902 are arranged between a substrate 310 and a scintillator 904 which is arranged on the side of the incident surface of the substrate 310. In addition, FIG. 3A shows a case in which the light-shielding layer 903 is arranged between the conversion element 902 and the scintillator 904 in the pixel PIXB. Also, FIG. 3B is similar to FIG. 3A in that the conversion element 901 and the conversion element 902 are arranged between the substrate 310 and the scintillator 904 which covers the side of the incident surface of the substrate 310. On the other hand, the arrangement of FIG. 3B shows a case in which the light-shielding layer 903 is arranged between the conversion element 902 and a scintillator 905 which is arranged on the side of the back surface opposite to the incident surface of the substrate 310 in the pixel PIXC.

The conversion element S of each pixel PIX is arranged on the substrate 310, which has an insulating property, such as a glass substrate or the like that is transparent to light beams emitted from the scintillators 904 and 905. Each pixel PIX includes a conductive layer 311 arranged on the substrate 310, an insulation layer 312 arranged on the conductive layer 311, a semiconductor layer 313 arranged on the insulation layer 312, an impurity semiconductor layer 314 arranged on the semiconductor layer 313, and a conductive layer 315 arranged on the impurity semiconductor layer 314. The conductive layer 311 forms a gate electrode of the transistor (for example, a TFT) forming the switch T. The insulation layer 312 is arranged to cover the conductive layer 311, and the semiconductor layer 313 is arranged, via the insulation layer 312, on a portion that forms the gate electrode of the conductive layer 311. The impurity semiconductor layer 314 is arranged on the semiconductor layer 313 so as to form the two main terminals (the source and the drain) of the transistor that forms the switch T. The conductive layer 315 forms a wiring pattern connected to each of the two main terminals (the source and the drain) of the transistor that forms the switch T. A part of the conductive layer 315 forms the column signal line Sig, and the other part of the conductive layer 315 forms the wiring pattern for connecting the conversion element S and the switch T.

Each pixel PIX further includes an interlayer insulating film 316 which covers the insulation layer 312 and the conductive layer 315. A contact plug 317 for connecting the portion forming the switch T of the conductive layer 315 is provided in the interlayer insulating film 316. In addition, each pixel PIX includes the conversion element S arranged on the interlayer insulating film 316. In the example shown in FIGS. 3A and 3B, each conversion element S is formed as an indirect-type photoelectric conversion element that converts the light converted from the radiation by the scintillators 904 and 905 into an electrical signal. In each conversion element S, a conductive layer 318, an insulation layer 319, a semiconductor layer 320, an impurity semiconductor layer 321, a conductive layer 322, and an electrode layer 325 are stacked on the interlayer insulating film 316. A protective layer 323 and an adhesive layer 324 are arranged on each conversion element S. The scintillator 904 is arranged on the adhesive layer 324 so as to cover the side of the incident surface of the substrate 310. The scintillator 905 is also arranged so as to cover the side of the back surface opposite to the incident surface of the substrate 310.

The conductive layer 318 forms the lower electrode of each conversion element S. Also, the conductive layer 322 and the electrode layer 325 form the upper electrode of each conversion element S. The conductive layer 318, the insulation layer 319, the semiconductor layer 320, the impurity semiconductor layer 321, and the conductive layer 322 form a MIS sensor as the conversion element S. For example, the impurity semiconductor layer 321 is formed by an n-type impurity semiconductor layer.

Each of the scintillators 904 and 905 can be formed by using materials such as GOS (gadolinium oxysulfide), CsI (cesium iodide), and the like. These materials can be formed by bonding, printing, vapor deposition, and the like. The same materials may be used for the scintillator 904 and the scintillator 905 or different materials may be used in accordance with the energy to be obtained.

Although this embodiment shows an example in which a MIS sensor is used as each conversion element S, the present invention is not limited to this. Each conversion element S may be, for example, a p-n photodiode or a PIN photodiode.

The arrangement of the light-shielding layer 903 which is arranged in correspondence with each conversion element 902 and used to shield the light entering from the scintillator 904 or scintillator 905 will be described next. In the arrangement shown in FIG. 3A, the conversion element 902 shown in the pixel PIXB includes the semiconductor layer 320, the conductive layer 318 forming a lower electrode which is arranged on the side of the incident surface of the substrate 310 of semiconductor layer 320, and the conductive layer 322 forming an upper electrode which is arranged on the side of the scintillator 904 of the semiconductor layer 320. The conductive layer 322 forming this upper electrode will function as the light-shielding layer 903. More specifically, by using a material, such as Al, Mo, Cr, Cu, or the like, which is opaque to light emitted by the scintillator 904 to form the conductive layer 322, the conductive layer 322 will function as the light-shielding layer 903. That is, the light-shielding layer 903 is arranged between the conversion element 902 and the scintillator 904 so that the conversion element 902 of the pixel PIXB will receive a smaller amount of light from the scintillator 904 than the conversion element 901. In addition, the conversion element 902 of the pixel PIXB is arranged to be able to receive light from the scintillator 905 in a manner similar to the conversion element 901 shown in the pixel PIXA. Furthermore, in the arrangement shown in FIG. 3B, the conversion element 902 shown in the pixel PIXC includes the semiconductor layer 320, the conductive layer 318 forming a lower electrode which is arranged on the side of the incident surface of the substrate 310 of the semiconductor layer 320, and the conductive layer 322 forming an upper electrode which is arranged on the side of the scintillator 904 of the semiconductor layer 320. The conductive layer 318 which forms this lower electrode will function as the light-shielding layer 903. More specifically, by using a material, such as Al, Mo, Cr, Cu, or the like, which is opaque to light emitted by the scintillator 905 to form the conductive layer 318, the conductive layer 322 will function as the light-shielding layer 903. That is, the light-shielding layer 903 is arranged between the conversion element 902 and the scintillator 905 so that the conversion element 902 of the pixel PIXC will receive a smaller amount of light from the scintillator 905 than the conversion element 901. In addition, the conversion element 902 of the pixel PIXC is arranged to receive light from the scintillator 904 in a manner similar to the conversion element 901 of the pixel PIXA.

On the other hand, in the conversion element 901 of the pixel PIXA, a material, such as ITO (indium tin oxide), which is transparent to the light emitted from the scintillator 904 is used for the conductive layer 318 and the electrode layer 325. This will allow different energy component signals to be obtained between the adjacent pixels PIXA and PIXB or PIXC. In this manner, the plurality of conversion elements S include the plurality of the conversion elements 901 and the plurality of the conversion elements 902 that have different sensitivities for detecting light emitted by at least one of the scintillator 904 or the scintillator 905.

In addition, although this embodiment showed an example in which the conductive layer 322 of the pixel PIXB and the conductive layer 318 of the pixel PIXC each have a single-layer structure, the present invention is not limited to this. For example, a transparent material and an opaque material may be stacked in each of the conductive layer 322 of the pixel PIXB and the conductive layer 318 of the pixel PIXC, and in such a case, the light shielding amount will be determined by the area of the opaque material. Also, although the conductive layer 322 of the pixel PIXB and the conductive layer 318 of the pixel PIXC each functioned as the light-shielding layer 903 in this embodiment, the arrangement of the light-shielding layer 903 is not limited to this. For example, in the pixel PIXB, the light-shielding layer 903 which is made of Al, Mo, Cr, Cu, or the like and is dedicated to shielding the light that enters from the scintillator 904 may be arranged in the protective layer 323. In such a case, the potential of the light-shielding layer 903 may be fixed to a predetermined potential and used.

In addition, in a case in which the light from the scintillator 905 is to be shielded in the manner of the pixel PIXC shown in FIG. 3B, the positions of the switch T and the column signal line Sig of the pixel PIXA that receives light from the scintillator 905 can be arranged closer to the side of the pixel PIXC. This kind of arrangement will increase the aperture ratio of the conversion element 901 in the pixel PIXA with respect to the scintillator 905.

In addition, the light-shielding layer 903 need not completely shield the light from the scintillator 904 or the scintillator 905 to the conversion element 902 in the above-described manner. Energy subtraction is possible as long as the amount of light received from the scintillator 904 or the scintillator 905 of the side on which the light-shielding layer 903 is arranged will differ between the adjacent pixels PIXA and PIXB or PIXC. In such a case, the percentage of the light which will enter the conversion element 902 of the pixel PIXB or PIXC from the light to be received by the conversion element 901 of the pixel PIXA can be checked in advance to allow correction to be performed by executing difference processing based on the output of the conversion element 901 as a reference.

As shown in FIGS. 3A and 3B, each of the column signal lines Sig is arranged so as to overlap a part of the corresponding pixel PIX in an orthogonal projection with respect to the incident surface of the substrate 310. Although this kind of arrangement is advantageous in the point that it increases the area of the conversion element S of each pixel PIX, it is disadvantageous in the point that it increases the capacitive coupling between the column signal line Sig and the conversion element S. If radiation enters the conversion element S and the potential of the conductive layer 318 as the lower electrode changes due to accumulation of charges in the conversion element S, crosstalk in which the potential of the column signal line Sig is changed due to the capacitive coupling between the column signal line Sig and the conversion element S will occur. FIGS. 4A to 4D each show a method for coping with such crosstalk. The number of pixels PIX that include the conversion elements 902 with the light-shielding layer 903 included in the conversion elements S, which are arrayed in the row direction intersecting with the column direction among the plurality of the conversion elements S, will be arranged to be the same for each row. In addition, the number of pixels PIX that include the plurality of conversion elements 902 included in the conversion elements S which are arrayed in the column direction among the plurality of conversion elements S will be arranged to be the same for each column. This kind of arrangement will allow the generation of artifacts caused by crosstalk to be suppressed on a row and column basis.

In addition, the radiation imaging apparatus 210 may have a function to automatically detect the start of radiation irradiation. In this case, for example, a signal from the conversion element S will be read out by operating each switch T to set the corresponding gate line Vg to ON/OFF, and the presence/absence of radiation irradiation will be determined based on the output signal. If the number of the pixels PIX that include the conversion element 902 including the light-shielding layer 903 changes for each row, the signal amount to be output for each row will change for each row, thus resulting in variation in the detection accuracy. Hence, as shown in FIGS. 4A to 4D, for the conversion element S which are arrayed in the row direction intersecting with the column direction among the plurality of the conversion elements S, the number of pixel PIX including the conversion elements 902 with the light-shielding layers 903 will be arranged to be the same for each row. Employing this kind of arrangement will stabilize the detection accuracy of the operation for automatically detecting the start of radiation irradiation.

Figure 4A:
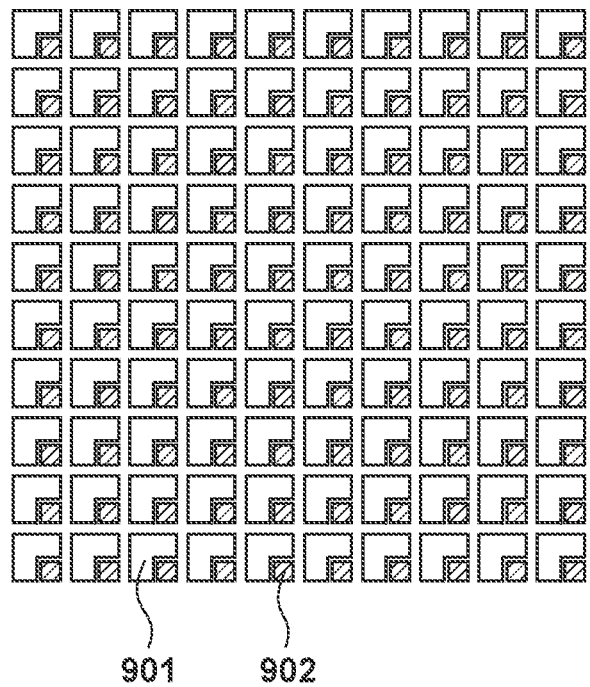
FIG. 4A is a view showing an example of the arrangement of the pixels of the radiation imaging apparatus of FIG. 1.
Figure 4B:
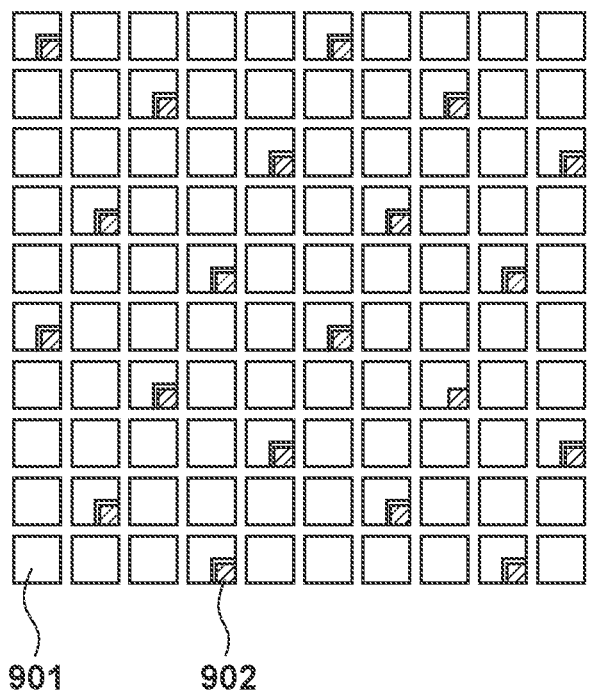
FIG. 4B is a view showing an example of the arrangement of the pixels of the radiation imaging apparatus of FIG. 1.
Figure 4C:
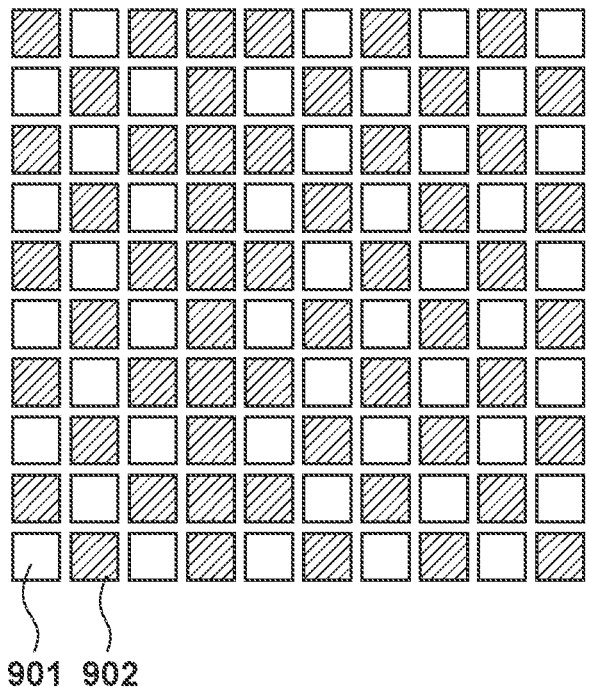
FIG. 4C is a view showing an example of the arrangement of the pixels of the radiation imaging apparatus of FIG. 1.
Figure 4D:
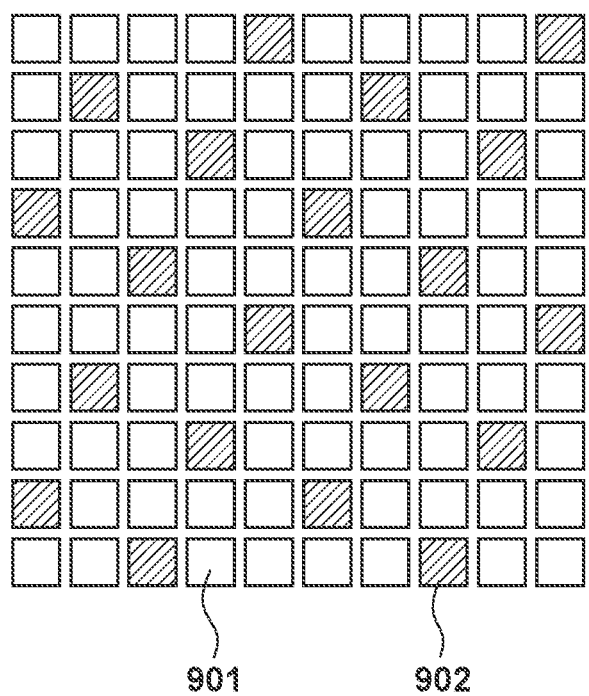
FIG. 4D is a view showing an example of the arrangement of the pixels of the radiation imaging apparatus of FIG. 1.

In addition, the density of the pixels PIX including the conversion elements 902 in each of the arrangement examples of the pixels PIX of FIGS. 4B and 4D is lower than each of the arrangement examples of the pixels PIX of FIGS. 4A and 4C. Since the light from the scintillator 905 enters the conversion element S via the substrate 310, the light will be dispersed due to the thickness of the substrate 310, and MTF (Modular Transfer Function) will decrease. Hence, even if the density of the pixels PIX including the conversion elements 902 is reduced, the resolution will not substantially decrease. That is, in a case in which each conversion element 902 is to receive the light emitted from the scintillator 905 which it faces via the substrate 310 among the two scintillators, the number of the pixels PIX including the conversion elements 902 may be smaller than the number of the pixels PIX including the conversion elements 901.

Figure 5:
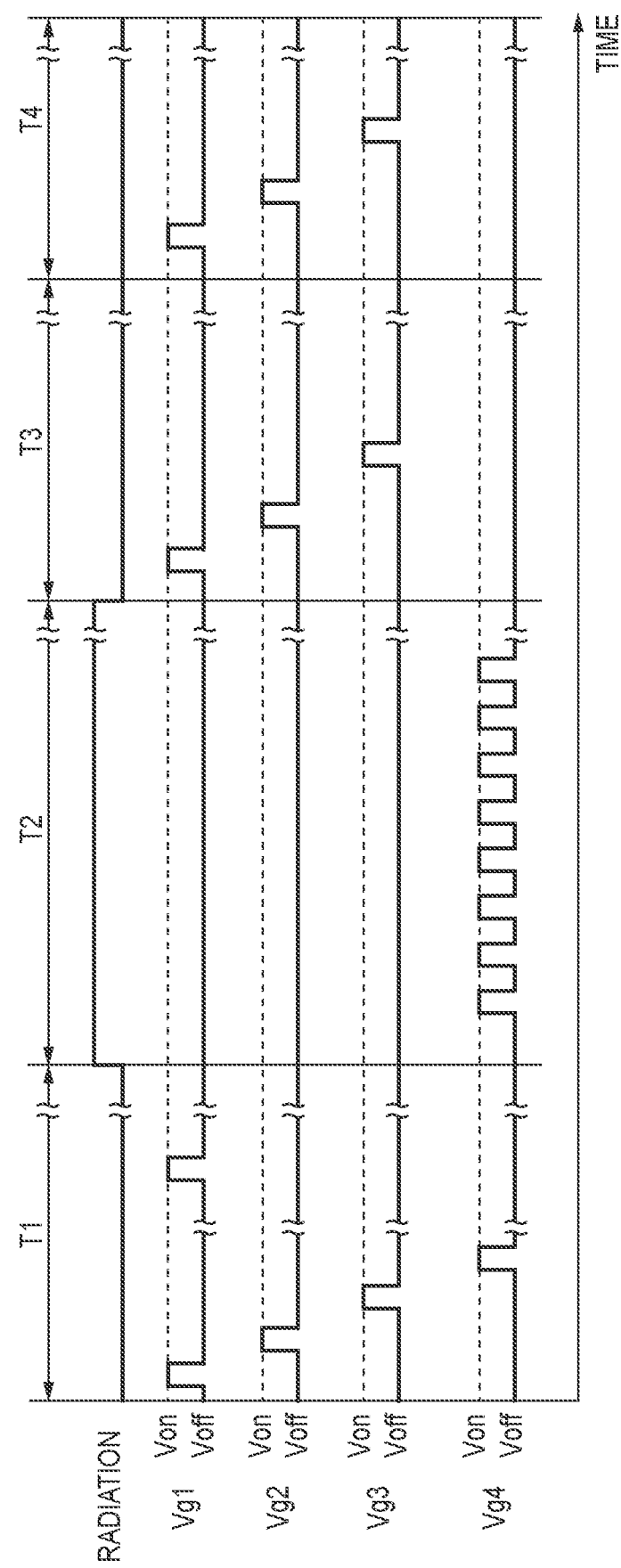
FIG. 5 is a timing chart showing an operation of the radiation imaging apparatus of FIG. 1.

The operation of the radiation imaging apparatus 210 will be described next with reference to FIG. 5. The operation of the radiation imaging system 200 is controlled by, for example, the computer 240. The operation of the radiation imaging apparatus 210 is controlled by the controller 214 under the control of the computer 240. A case in which the light-shielding layer 903 is arranged between each conversion element 902 and the scintillator 904 in a manner similar to the arrangement shown in FIG. 3A will be described here.

During a period T1, a gate signal Von is supplied to each of the gate lines Vg1 to Vg4 to cause the switches T to sequentially perform an ON operation, and a reset operation that resets each conversion element S. Next, when radiation irradiation is started, the start of radiation irradiation can be detected by, for example, a detection circuit 216 that detects a current flowing in the bias line Bs, each column signal line Sig, or the like. However, the present invention is not limited to this, and the start of radiation irradiation may be detected based on a signal supplied from the computer 240 to the radiation imaging apparatus 210. When the radiation irradiation is started, the radiation imaging apparatus 210 shifts the process from the period T1 to a period T2.

The period T2 will be described next. The period T2 is a period in which radiation irradiation is performed. For example, the period T2 is a period from when the start of radiation irradiation is detected to when the radiation dose reaches an appropriate dose for obtaining the radiation image data. Hence, the period T2 can also be called a period for monitoring the radiation irradiation dose. That is, in this embodiment, it can be said that the radiation imaging apparatus 210 has an automatic exposure control (AEC) function. A case in which the conversion elements S41 to S44 connected to the gate line Vg4 are used (selected) as measuring elements for measuring (monitoring) the incident radiation dose will be described.

During the period T2, the gate signal Von is applied to the gate line Vg4 to cause switches T41 to T44 to execute an ON operation, and the signals accumulated in the conversion elements S41 to S44 are sequentially read out. Also, a gate signal Voff is supplied to each of the gate lines Vg1 to Vg3 so that switches T11 to T14, switches T21 to T24, and switches T31 to T34 will be turned off. This will cause the conversion elements S11 to S14, the conversion elements S21 to S24, and the conversion elements S31 to S34 to accumulate charges based on the light beams converted from the incident radiation beams by the scintillators 904 and 905.

Since a high energy component of the radiation will be absorbed and converted into light by the scintillator 905 after being transmitted through an object (not shown) and the scintillator 904, the incident radiation dose of the scintillator 905 will decrease. Hence, the signal value of each signal corresponding to the light converted by the scintillator 905 will decrease, and there is a possibility that the signal will be buried in, for example, a noise such as an offset signal of the conversion element S or the switch T or the variation of such noise in the surface. As a result, the accuracy at which a signal based on a high energy component of the radiation is obtained will decrease, and the image quality of the generated energy subtraction image may degrade.

Hence, in this embodiment, during radiation irradiation, the controller 214 will obtain a signal corresponding to the light converted from the radiation by the scintillator 905, in other words, a signal corresponding to a high energy component of the radiation. That is, during the period T2 when radiation irradiation is performed, the controller 214 will obtain signals output from the conversion elements S42 and S44 that are used as the measuring elements selected among the conversion elements 902 which receive the light converted by the scintillator 905. Based on these signals corresponding to the light converted from the radiation by the scintillator 905, the controller 214 will output a signal to stop the radiation irradiation performed on the radiation imaging apparatus 210.

More specifically, the controller 214 will determine whether a cumulative value of the signals corresponding to the light converted from the radiation by the scintillator 905 has reached a preset setting value. The controller 214 will output a stop signal for stopping the radiation irradiation to the irradiation controller 220 in accordance with the fact that the cumulative value of the signals corresponding to the light converted from the radiation by the scintillator 905 has reached the setting value. The controller 214 may transmit the stop signal to the irradiation controller 220 via the computer 240 or may transmit the stop signal directly to the irradiation controller 220 and the radiation source 230. This setting value can be preset based on, for example, the noise level of the pixel PIX, such as the noise level of the conversion element S or the switch T (to be simply referred to as "the noise level of the conversion element S" here) when radiation irradiation is not performed. For example, this setting value may be set to a value which is five times or more than the signal value corresponding to the noise level of the conversion element S (an SNR of 5 or more). Alternatively, the setting value may be set to a value which is ten times or more than the signal value corresponding to the noise level of the conversion element S (an SNR of 10 or more). Furthermore, the setting value may be set to a value which is twenty times or more than the signal value corresponding to the noise level of the conversion element S (an SNR of 20 or more). This will allow the signals corresponding to the light converted from the radiation by the scintillator 905 to be sufficiently ensured and the influence from the noise can be suppressed. As a result, it will be possible to suppress the degradation of the image quality of the obtained energy subtraction image.

In addition, during the period T2, each signal of the light converted from the radiation by the scintillator 904, in other words, each signal caused by a low energy component of the radiation (signals output from the conversion elements S41 and S43 used as the measuring elements) may also be similarly monitored. The signal corresponding to the light converted by the scintillator 904 can include a larger amount of light that reached the conversion element S than the signal corresponding to the light converted by the scintillator 905. Hence, each signal (charge) corresponding to the light converted by the scintillator 904 may become saturated before the cumulative value of the signals obtained in correspondence with the light converted by the scintillator 905 reaches the above-described setting value. If the signal is saturated, it may degrade the image quality of the radiation image to be obtained. In this embodiment, since the conversion elements 901 including the conversion elements S41 and S43 receive both light beams converted by the scintillators 904 and 905, it can increase the possibility of further saturation. Hence, the controller 214 will also obtain a cumulative value of the signals corresponding to the light beams from the scintillators 904 and 905, and determine whether the cumulative value has reached a setting value preset based on the saturation levels of the conversion elements S41 and S43 selected as the measuring elements from the conversion elements 901. That is, the controller 214 will not only obtain each signal corresponding to the light converted by the scintillator 905 but also each signal corresponding to the light converted by the scintillator 904, and output, based on these signals, the stop signal for stopping radiation irradiation. Since the saturation dose will change based on the gain or the like of the readout circuit 113 here, the controller 214 may also include a plurality of setting values corresponding to imaging conditions in, for example, a memory or the like in the controller 214.

These two kinds of setting values may be set to separate values as described above. However, the present invention is not limited to this, and the two kinds of setting values may be set to the same value. For example, a setting value may be set to each of the signal value of the saturation level estimated from the signals of conversion elements 901 and a median value of the signal value of the noise level estimated from the signals of the conversion elements 902.

In this manner, the radiation imaging apparatus 210 controls radiation irradiation based on each signal corresponding to the light converted from high energy radiation by the scintillator 905. This can increase the accuracy of the signal caused by high energy radiation. Furthermore, each signal corresponding to the light converted from low energy radiation by the scintillator 904 is also measured. This will suppress a state in which the conversion elements 901 will become saturated, and prevent unnecessary exposure, due to redoing of imaging, to a patient or the like. As a result, it will be possible to obtain the radiation imaging apparatus 210 that can obtain an energy subtraction image with improved accuracy.

Periods T3 and T4 of FIG. 5 will be described next. The period T3 is a period in which signals accumulated in the conversion elements S11 to S14, the conversion elements S21 to S24, and the conversion elements S31 to S34 in accordance with the light beams converted from the radiation beams are read out after the radiation irradiation has ended. The gate signal Von, which is used to cause the switches T11 to T14, the switches T21 to T24, and the switches T31 to T34 to be sequentially turned on, is supplied to each of the gate lines Vg1 to Vg3 to execute a readout operation. At this time, the gate signal Voff is supplied to the gate line Vg4 to turn off the switches T41 to T44.

The period T4 is a period for obtaining offset data. The conversion elements S will continue to accumulate dark charges even in a state in which radiation irradiation is not performed. Hence, the controller 214 will obtain offset image data by performing an operation similar to that performed when radiation image data is obtained without radiation irradiation. By subtracting the offset image data from the radiation image data, an offset component due to the dark charges can be removed.

In this manner, the periods T3 and T4 can be a period in which the controller 214 will cause the conversion elements 901 and the conversion elements 902 to output the signals for generating an energy subtraction image after the radiation irradiation operation. The signals output from the conversion elements 901 and the conversion element 902 are transmitted to, for example, the signal processor 241 of the computer 240. Based on the signals output from the respective conversion elements 901 and the signals output from the respective conversion elements 902, the signal processor 241 will generate an energy subtraction image and display the generated image on a display (not shown) which is connected to the computer 240. As a result, the user can observe a radiation image (subtraction image).

An image processing procedure according to this embodiment will be described next with reference to FIGS. 6A and 6B. Here, it will be assumed that, in the arrangement shown in FIG. 3B, radiation will enter from the upper side of the drawing, and each conversion element 902 will be shielded from the light from the scintillator 905 and receive light caused by low energy radiation from the scintillator 904. In addition, the radiation image data output from each conversion element 901 may be referred to as double-sided image data, the radiation image data output from each conversion element 902 may be referred to as single-sided image data.

First, in step S910, upon detecting the start of radiation irradiation as described above, the controller 214 will shift to the process of step S930. In step S930, the controller 214 will start obtaining the signals from the measuring elements (for example, the conversion elements S41 to S44 described above) selected, from the conversion elements S, for measuring the incident radiation dose to obtain a radiation image (energy subtraction image). In addition, to obtain the radiation image data, the conversion elements S other than the measuring elements will start performing an accumulation operation to accumulate charges corresponding to the light beams converted from the incident radiation.

Next, the controller 214 obtains each signal corresponding to the light converted from the radiation by the scintillator 905 which receives the radiation transmitted through the scintillator 904, and determines, based on this signal, whether to continue or stop radiation irradiation (step S950). Here, as described above, the conversion element 901 will output a signal corresponding to light beams converted by the scintillator 904 and the scintillator 905, and the conversion element 902 outputs a signal corresponding to the light converted by the scintillator 904. Hence, the controller 214 will obtain, based on a difference between the signals output from the measuring elements (for example, the conversion elements S41 and S43) selected from the conversion elements 901 and the signals output from the conversion element 902 (for example, the conversion elements S42 and S44), a signal corresponding to the light converted by the scintillator 905.

In addition, as described above, the controller 214 may obtain a signal not only from the scintillator 905, but also a signal corresponding to the light converted from the radiation by the scintillator 904, and may determine, based on this signal, whether to continue or stop the radiation irradiation (step S940). Here, each conversion element 901 will output a signal corresponding to the light beams converted by the scintillator 904 and the scintillator 905, and each conversion element 902 will output a signal corresponding to the light converted by the scintillator 904. Hence, the controller 214 may use both the signals output from the measuring elements (for example, the conversion elements S41 and S43) selected from the conversion elements 901 and the signals output from the conversion elements 902 (for example, the conversion elements S42 and S44) to perform the determination of step S940. Alternatively, the controller 214 may perform the determination of step S940 by using only the signals output from the measuring elements (for example, the conversion elements S41 and S43) selected from the conversion elements 901.

Figure 6A:
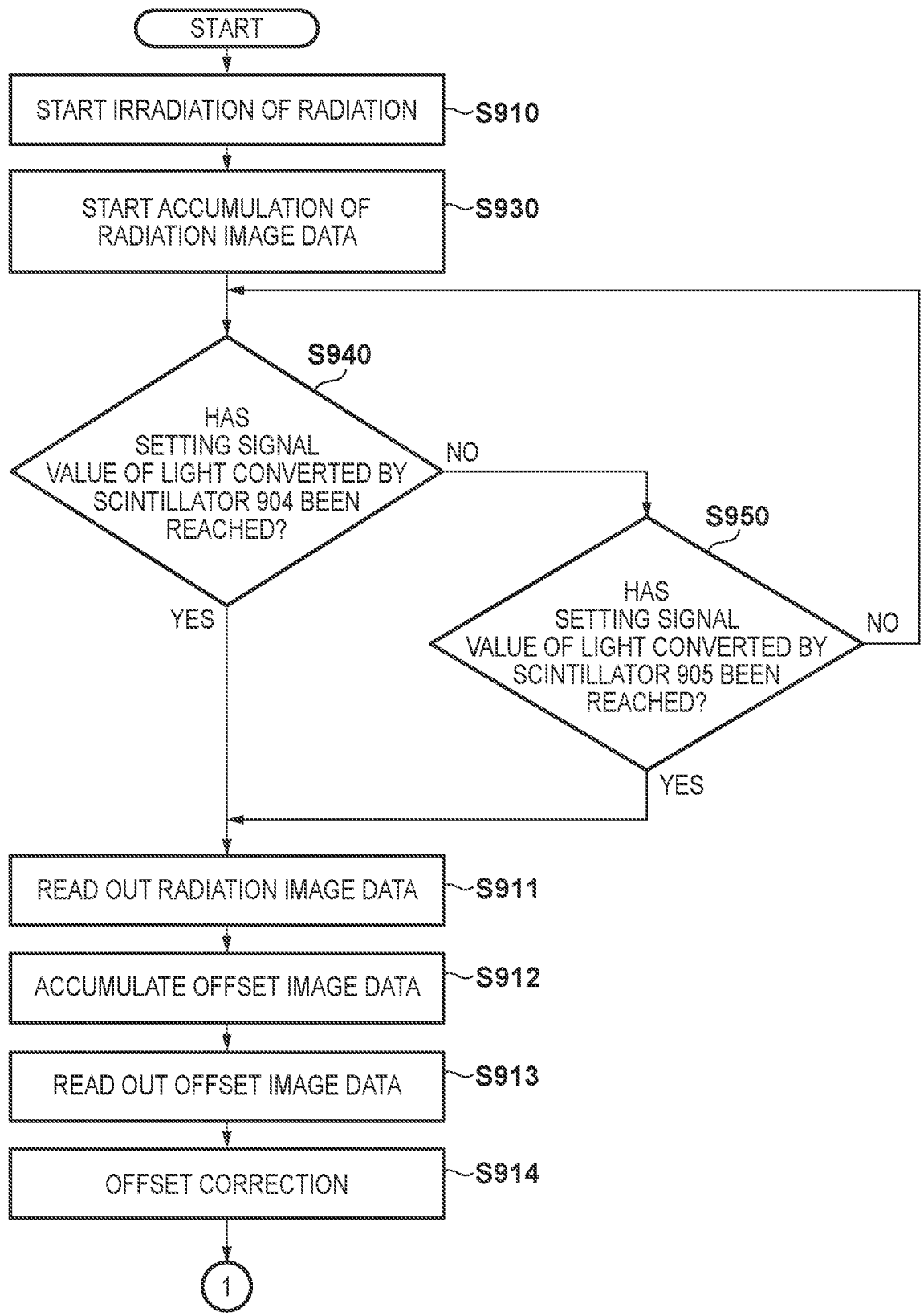
FIG. 6A is a flowchart showing the procedure of the operation of the radiation imaging apparatus of FIG. 1.
Figure 6B:
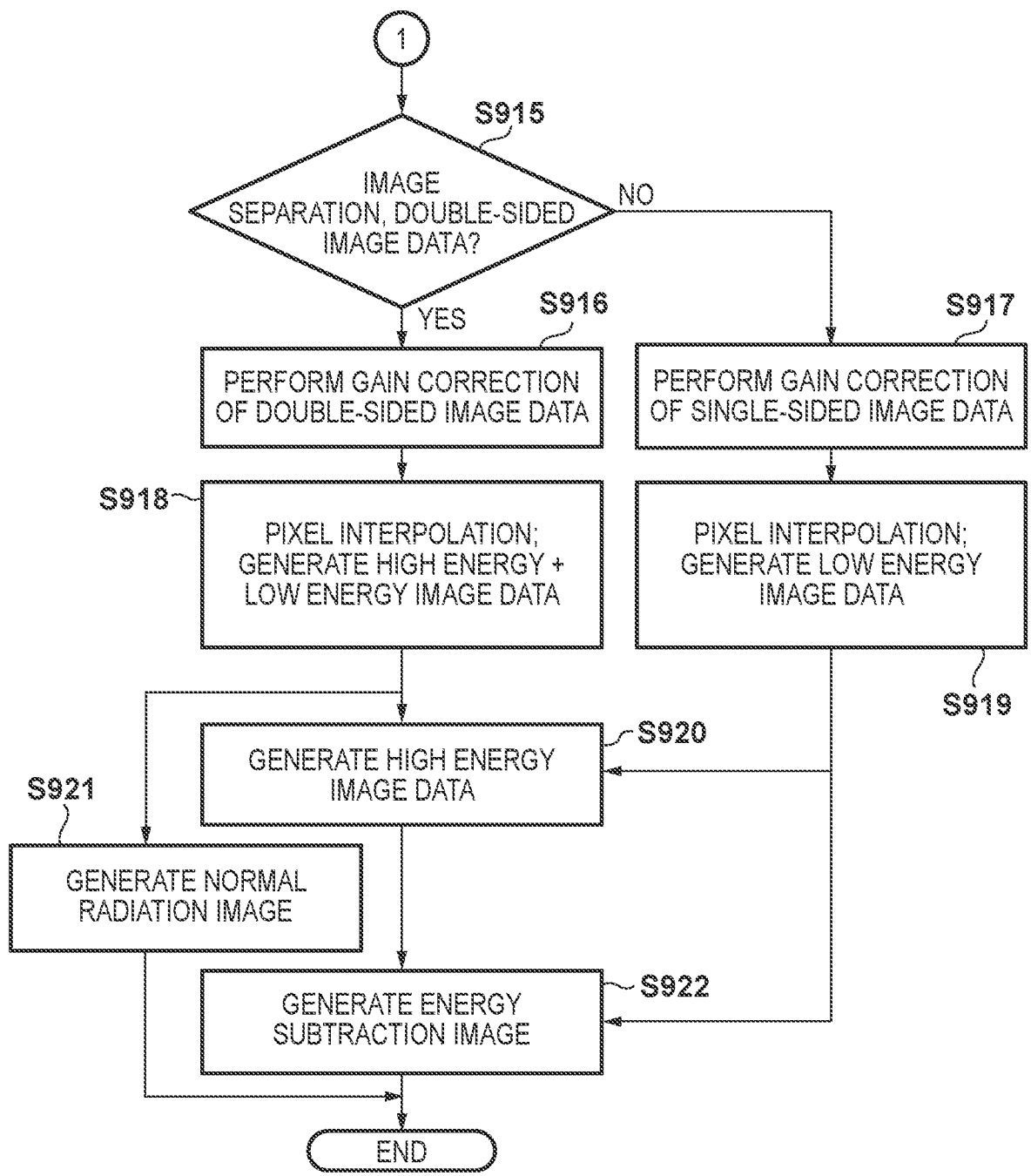
FIG. 6B is a flowchart showing the procedure of the operation of the radiation imaging apparatus of FIG. 1.

The determination of step S950 and the determination of step S940 may be performed alternately in the manner shown in FIG. 6A until it is determined in step S950 or S940 that one of the respective signal values has reached the corresponding setting value (NO in step S950 or S940). In addition, if the determination of step S950 and the determination of step S940 are to be performed, the determination of step S940 which has high sensitivity may be performed first, that is, immediately after the start of radiation irradiation as shown in FIG. 6A, in consideration of a case in which radiation irradiation is accidently performed at a very high dose due to a setting mistake. When the controller 214 has determined in step S950 or S940 that one of the respective signal values has reached the corresponding setting value (YES in step S950 or S940), the controller 214 will output a stop signal to stop the radiation irradiation and shift the process to step S911. The radiation source 230 will stop the radiation irradiation in response to the stop signal.

In step S911, the controller 214 will cause the signals generated by the conversion elements S to be output via the driving circuit 114 and the readout circuit 113, and read out the radiation image data. The radiation image data is output to the computer 240 in this step S911. Next, in step S912, the controller 214 executes an accumulation operation to obtain offset image data, and in step S913, the offset image data is read out by the driving circuit 114 and the readout circuit 113 and output to the computer 240.

Next, the signal processor 241 of the computer 240 performs offset correction by subtracting the offset image data obtained in step S913 from the radiation image data obtained in step S911. Next, in step S915, the signal processor 241 separates the radiation image data that has undergone the offset correction into the radiation image data output from the conversion elements 901 and the radiation image data output from the conversion elements 902.

Next, in step S916, the signal processor 241 uses gain correction image data, which is obtained by executing imaging in a state without an object, to perform gain correction of the double-sided image data. In addition, in step S917, the signal processor 241 uses the gain correction image data to perform gain correction of the single-sided image data.

After the execution of gain correction, in step S918, the signal processor 241 performs pixel interpolation to supplement each pixel PIX that does not include the conversion element 901, in other words, the missing double-sided image data of each pixel PIX including the conversion element 902. In a similar manner, in step S919, the signal processor 241 performs pixel interpolation to supplement the pixel PIX that does not include the conversion element 902, in other words, the missing single-sided image data of each pixel PIX including the conversion element 901. The pixel interpolation operations performed in steps S918 and S919 will be described with reference to FIGS. 7A and 7B. The arrangement of a case in which there are more pixels PIX including the conversion elements 901 than the pixels PIX including the conversion elements 902 as shown in FIG. 4D will be exemplified here.

Figure 7A:
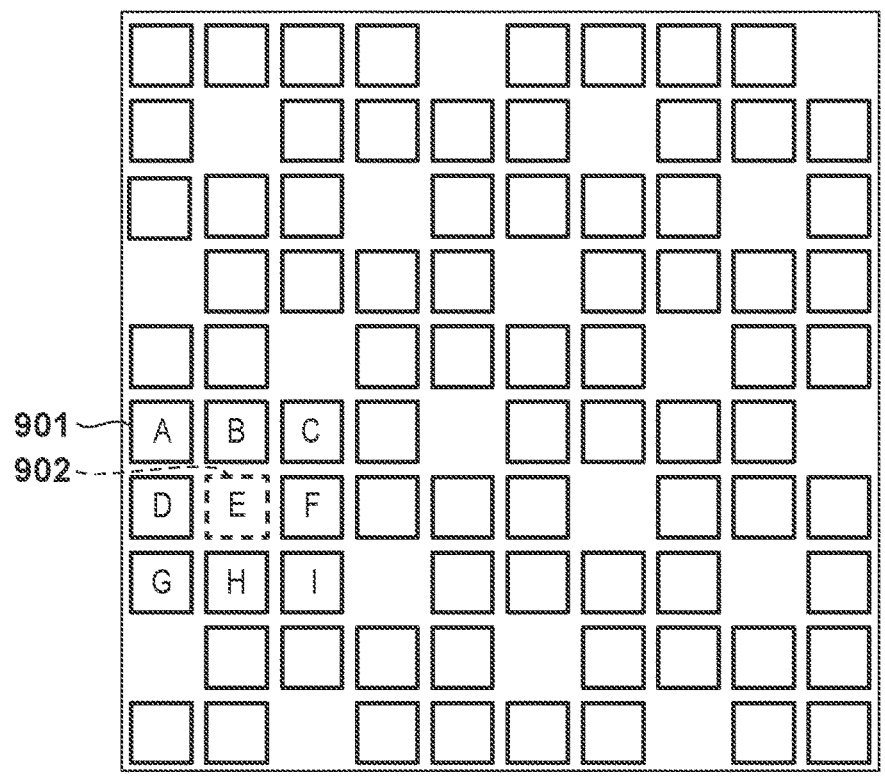
FIG. 7A is a view showing an example of pixel interpolation of the radiation imaging apparatus of FIG. 1.

Pixel interpolation of double-sided image data will be described first with reference to FIG. 7A. The double-sided image data of a pixel E including the conversion element 902 for outputting single-sided image data will be interpolated by using the double-sided image data of pixels A, B, C, D, F, G, H, and I each adjacent to the pixel E and each including the conversion element 901 for outputting double-sided image data. For example, the signal processor 241 may use the average value of the double-sided image data of the eight pixels adjacent to the pixel E to interpolate the double-sided image data of the pixel E. Also, for example, the signal processor 241 may use the average value of the double-sided image data of some of the adjacent pixels such as the pixels B, D, F, and H to interpolate the double-sided image data of the pixel E. By performing pixel interpolation in step S918, radiation image data generated from the high energy component and the low energy component of the radiation of each pixel PIX will be generated.

Figure 7B:
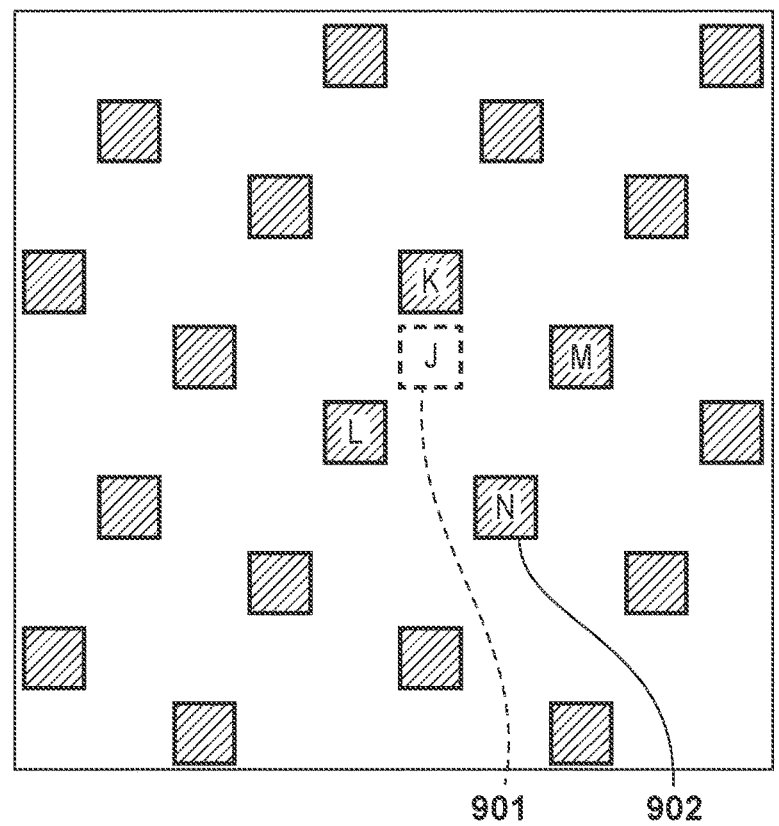
FIG. 7B is a view showing an example of the pixel interpolation of the radiation imaging apparatus of FIG. 1.

Pixel interpolation of single-sided image data will be described next with reference to FIG. 7B. The single-sided image data of a pixel J including the conversion element 901 for outputting double-sided image data will be interpolated by using the single-sided image data of pixels K, L, M, and N each adjacent to the pixel J and each including the conversion element 902 for outputting single-sided image data. For example, the signal processor 241 may use the average value of the single-sided image data of the four pixels adjacent to the pixel J to interpolate the single-sided image data of the pixel J. In this case, for example, the distance from the arrangement position of the pixel J to the pixel K and the distance from the arrangement position of the pixel J to the pixel N are different. Hence, averaging may be performed by weighting the single-sided image data output from each of the pixels K, L, M, and N in accordance with the distance. In step S919, pixel interpolation can be performed to generate radiation image data which is generated based on the low energy component of the radiation of each pixel PIX.

Next, in step S920, the signal processor 241 generates radiation image data based on a high energy component of the radiation. As described above, in a case in which the light-shielding layer 903 is arranged between each conversion element 902 and the scintillator 905, the single-sided image data will be radiation image data generated based on a low energy component. Also, the double-sided image data will be radiation image data which includes both a high energy component and a low energy component. Hence, radiation image data based on a high energy component can be generated by subtracting the single-sided image data which has undergone pixel interpolation from the double-sided image data which has undergone pixel interpolation.

Alternatively, in a case in which the light-shielding layer 903 is arranged on the radiation incident side of the conversion element 902, the single-sided image data will be radiation image data based on a high energy component. Hence, radiation image data based on a low energy component can be generated by subtracting the single-sided image data which has undergone pixel interpolation from the double-sided image data which has undergone pixel interpolation.

Since a radiation image based on a high energy component is based on a component of radiation that could not be completely absorbed by the scintillator 904 on the radiation incident side, the amount of light from the scintillator 905 is less than the amount of light from the scintillator 904. Hence, if radiation image data based on a high energy component is generated by subtracting the single-sided image data from the double-sided image data, the noise of the radiation image data based on a low energy component will be superimposed on the radiation image data based on the high energy component. As a result, the S/N ratio of the radiation image data based on the high energy component will decrease. Hence, the radiation incident side of each conversion element 902 will be shielded so that the double-sided image data will be image data based on a high energy component plus a low energy component and the single-sided image data will be image data based on a high energy component. Generating a low energy image by subtracting the single-sided image data from the double-sided image obtained in this manner can improve the S/N ratio.

In step S922, the signal processor 241 generates an energy subtraction image. More specifically, the signal processor 241 obtains a difference between the signal output from each conversion element 902 and the difference between the signal output from each conversion element 901 and the signal output from each conversion element 902 obtained in step S920. This will generate an energy subtraction image which is a difference between the radiation image data based on a high energy component and the radiation image data based on a low energy component.

In addition, the signal processor 241 may generate, based on the double-sided image data output from each conversion element 901 in step S918, a normal radiation image without performing energy subtraction in step S920. Each conversion element 901 receives the light from the scintillator 904 on the radiation incident side and the light from the scintillator 905 on a side opposite to the radiation incident side. As a result, a high S/N ratio can be obtained in a normal radiation image than in a case in which only the light emitted by one of the scintillators is received.

A radiation imaging apparatus, such as that disclosed in PTL 1, in which photoelectric conversion elements that receive only the light from a scintillator on the radiation incident side and photoelectric conversion elements that receive only the light from a scintillator on the opposite side are arranged will be considered here. In such an apparatus, a normal radiation image can be generated by obtaining a difference between the two signals output from each set of these two photoelectric conversion elements to generate an energy subtraction image and adding the two signals. However, since two photoelectric conversion elements will be required to generate one pixel data, it will complicate the structure and may increase the manufacturing cost. Also, since the size of each photoelectric conversion element will become small, it may decrease the S/N ratio of each obtained signal. In addition, since a noise superimposed on each signal will also be added when the two signals are to be added to generate a normal radiation image, it may decrease the S/N ratio. On the other hand, in an arrangement as shown in FIGS. 3A and 3B, the light-shielding layer 903 for shielding the light from the scintillator 904 or the scintillator 905 will be arranged on only some of the pixel PIX including the conversion elements 902 among the plurality of pixels PIX. That is, since the light-shielding layer 903 need only be added to some of the pixels PIX, the structure will not become complicated, and a radiation imaging apparatus that can obtain an energy subtraction image can be implemented with a suppressed manufacturing cost. In addition, since each conversion element 901 will receive the light beams emitted from the scintillator 904 and the scintillator 905, the sensitivity toward incident radiation will improve and, as a result, the image quality of the radiation image to be obtained can be improved. Furthermore, even when a normal radiation image is to be generated, a radiation image will be generated based on signals generated by receiving light emitted from the two scintillators 904 and 905. Hence, compared to a structure as that disclosed in PTL 1, the S/N ratio obtained when a normal radiation image is captured will improve.

Also, in this embodiment, one imaging panel 212 can be used to record a radiation image based on two different energy components of the radiation by performing one radiation irradiation operation (one shot method) on an object. Hence, compared to a radiation imaging apparatus that uses two imaging panels to generate an energy subtraction image, a small number of components will be required for the radiation imaging apparatus, thereby reducing the manufacturing cost. In addition, since the weight of the radiation imaging apparatus 210 can be reduced, a radiation imaging apparatus that can be easy to use for a user who requires portability can be implemented. Also, since one imaging panel is used to generate an energy subtraction image, it will be possible to implement a radiation imaging apparatus in which the problem of a positional shift between the photoelectric conversion elements of the two imaging panels will not occur. Furthermore, it will be possible to implement a radiation imaging apparatus that can generate a radiation image with a high S/N ratio in not only the generation of an energy subtraction image but also in the generation of a normal radiation image.

In addition, as described above, during radiation irradiation, the controller 214 will measure each signal emitted from the scintillator 905 which has a smaller amount of light converted from radiation. Hence, a signal corresponding to the light converted by the scintillator 905 can be obtained without the signal becoming buried in the noise. As a result, the image quality of the obtained subtraction image will improve, and it will be possible to improve, for example, the accuracy of image diagnosis by a doctor.

Figure 8:
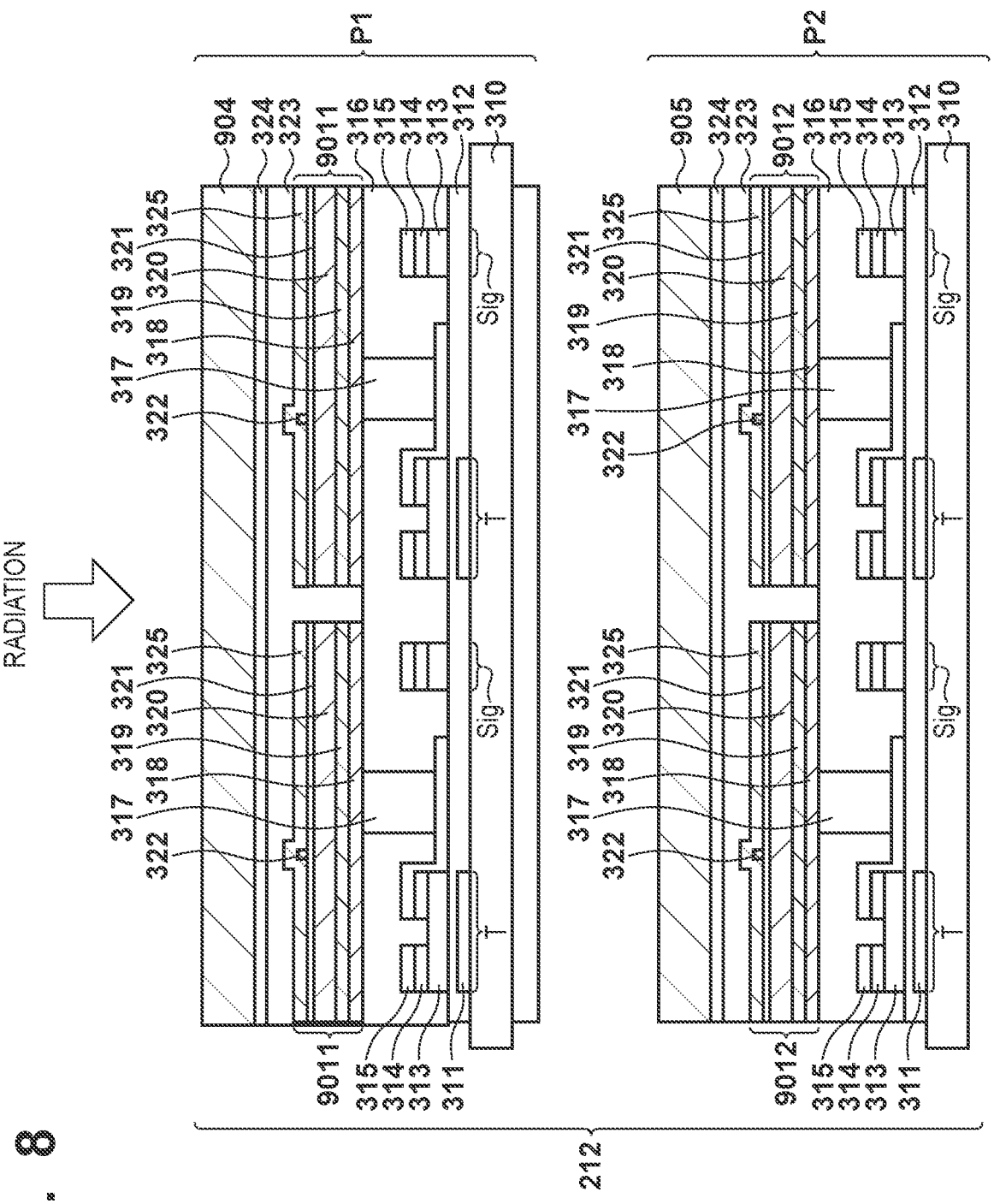
FIG. 8 is a view showing an example of the structure of a section of the pixels of the radiation imaging apparatus of FIG. 1.

The above-described embodiment showed an example in which the scintillator 904 and 905 are arranged to cover both sides of one substrate 310 as the imaging panel 212 of the radiation imaging apparatus 210. However, the present invention is not limited to this. For example, as shown in FIG. 8, two imaging panels P1 and P2 may be applied as the imaging panel 212 of the radiation imaging apparatus 210. The two imaging panels P1 and P2 may be panels which have the same structure. In addition, in this case, each pixel PIX may not include the light-shielding layer 903 as described above. That is, in the arrangement shown in FIG. 8, each conversion element S can have an arrangement equal to the conversion element 901 shown in FIGS. 3A and 3B. Also, in the arrangement shown in FIG. 8, a scintillator arranged on the imaging panel P1 which is to be arranged on the radiation incident side corresponds to the above-described scintillator 904, and a scintillator arranged on the other imaging panel P2 corresponds to the above-described scintillator 905.

In the arrangement shown in FIG. 8, the controller 214 will also obtain each signal corresponding to the light converted from radiation by the scintillator 905, and determine, based on this signal, whether to stop the radiation irradiation to the radiation imaging apparatus 210. That is, the controller 214 can obtain a signal output from each conversion element 9012 arranged on the imaging panel P2 and determine, based on the signal output from each conversion element 9012, whether to continue or stop the radiation irradiation operation. At this time, to prevent the light converted by the scintillator 904 of the imaging panel P1 from entering each conversion element 9012, the substrate 310 of the imaging panel P1 may be, for example, opaque to the light generated by the scintillator 904. Also, for example, each of the imaging panel P1 and the imaging panel P2 may be covered by a light-shielding film or the like. Furthermore, in a manner similar to that described above, the determination as to whether to continue or stop the radiation irradiation operation may be performed by also using, in parallel, each signal output from each conversion element 9011 arranged on the imaging panel P1.

In the arrangement shown in FIG. 8 as well, each signal corresponding to the light converted from a high energy component of the radiation by the scintillator 905 can be obtained, in a manner similar to the above-described embodiment, without the signal becoming buried in the noise. As a result, it will be possible to improve the image quality of the obtained energy subtraction image.

According to the above-described means, a technique advantageous in suppressing image quality degradation of an energy subtraction image can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus that comprises a first scintillator, a second scintillator which receives radiation transmitted through the first scintillator, a plurality of conversion elements, and a controller, wherein
the plurality of conversion elements include a plurality of first conversion elements and a plurality of second conversion elements with different sensitivities for detecting light emitted from at least one of the first scintillator or the second scintillator, and
during radiation irradiation, the controller is configured to obtain, from a signal output from not less than one measuring element configured to measure a dose of incident radiation among the plurality of first conversion elements and the plurality of second conversion elements, a first signal corresponding to light converted from radiation by the second scintillator among the first scintillator and the second scintillator, and
output, based on the first signal, a stop signal configured to stop the radiation irradiation to the radiation imaging apparatus, and
after the radiation irradiation, the controller is configured to cause the plurality of first conversion elements and the plurality of second conversion elements to output signals configured to generate an energy subtraction image.

2. The radiation imaging apparatus according to claim 1, wherein during the radiation irradiation, the controller is configured to
obtain, from the signal output from the measuring element, at least a second signal corresponding to light converted from radiation by the first scintillator, and
output the stop signal based on the first signal and the second signal.

3. The radiation imaging apparatus according to claim 2, wherein the second signal is a signal corresponding to the light converted from radiation by the first scintillator and the light converted from radiation by the second scintillator.

4. The radiation imaging apparatus according to claim 2, wherein the controller is configured to output the stop signal in response to one of a cumulative value of the first signal reaching a first setting value preset based on noise levels of the plurality of conversion elements and a cumulative value of the second signal reaching a second setting value preset based on saturation levels of the plurality of conversion elements.

5. The radiation imaging apparatus according to claim 4, wherein during the radiation irradiation, the controller is configured to alternately perform a first determination for determining whether the cumulative value of the first signal has reached the first setting value and a second determination for determining whether the cumulative value of the second signal has reached the second setting value.

6. The radiation imaging apparatus according to claim 5, wherein the controller is configured to alternately perform, in response to the start of the radiation irradiation, the first determination and the second determination after the second determination has been performed.

7. The radiation imaging apparatus according to claim 1, wherein the controller is configured to output the stop signal in response to a cumulative value of the first signal reaching a first setting value preset based on noise levels of the plurality of conversion elements.

8. The radiation imaging apparatus according to claim 7, wherein the first setting value is a value not less than 10 times a signal value corresponding to the noise levels of the plurality of conversion elements.

9. The radiation imaging apparatus according to claim 1, wherein the radiation imaging apparatus further comprises a substrate on which the plurality of conversion elements are arranged,
the first scintillator is arranged to cover a first surface of the substrate,
the second scintillator is arranged to cover a second surface on a side opposite to the first surface of the substrate,
the plurality of first conversion elements are arranged to receive light beams from the first scintillator and the second scintillator,
the plurality of second conversion elements are arranged to receive light from the second scintillator and include a light shielding layer between the first scintillator and each of the plurality of the second conversion elements so as to reduce an amount of light that can be received from the first scintillator than the plurality of first conversion elements,
the measuring element includes a first measuring element selected from the plurality of first conversion elements and a second measuring element selected from the plurality of second conversion elements, and
the controller is configured to obtain the first signal based on one of signals output from the first measuring element and the second measuring element and a signal output from the second measuring element.

10. The radiation imaging apparatus according to claim 9, wherein the controller is configured to obtain, as the first signal, the signal output from the second measuring element.

11. The radiation imaging apparatus according to claim 10, wherein the second measuring element does not receive the light from the first scintillator.

12. The radiation imaging apparatus according to claim 9, wherein the plurality of conversion elements are arranged between the first surface and the first scintillator, and include a semiconductor layer, a first electrode which is arranged on a side of the first surface of the semiconductor layer, and a second electrode which is arranged on as side of the first scintillator of the semiconductor layer, and
in the plurality of second conversion elements, the second electrode functions as the light-shielding layer.

13. The radiation imaging apparatus according to claim 1, wherein the radiation imaging apparatus further includes a substrate on which the plurality of conversion elements are arranged,
the first scintillator is arranged to cover a first surface of the substrate,
the second scintillator is arranged to cover a second surface on a side opposite to the first surface of the substrate,
the plurality of first conversion elements are arranged to receive light beams from the first scintillator and the second scintillator,
the plurality of second conversion elements are arranged to receive light from the first scintillator and include a light shielding layer between the second scintillator and each of the plurality of the second conversion elements so as to reduce an amount of light which can be received from the second scintillator than the plurality of first conversion elements,
the measuring element includes a first measuring element selected from the plurality of first conversion elements and a second measuring element selected from the plurality of second conversion elements, and the controller is configured to obtain the first signal based on signals output from the first measuring element and the second measuring element.

14. The radiation imaging apparatus according to claim 13, wherein the controller is configured to obtain the first signal based on a difference between the signal output from the first measuring element and the signal output from the second measuring element.

15. The radiation imaging apparatus according to claim 13, wherein the plurality of conversion elements are arranged between the first surface and the first scintillator, and include a semiconductor layer, a first electrode which is arranged on a side of the first surface of the semiconductor layer, and a second electrode which is arranged on as side of the first scintillator of the semiconductor layer, and in the plurality of second conversion elements, the first electrode functions as the light-shielding layer.

16. The radiation imaging apparatus according to claim 1, wherein the radiation imaging apparatus further includes a first substrate on which the plurality of first conversion elements are arranged and a second substrate on which the plurality of second conversion elements are arranged, the first substrate and the second substrate are arranged to overlap each other, the first scintillator is arranged to cover the first substrate, the plurality of first conversion elements receive light from the first scintillator, the second scintillator is arranged to cover the second substrate, the plurality of the second conversion elements receive light from the second scintillator, and the controller is configured to obtain, as the first signal, the signal output from the measuring element selected among the plurality of the second conversion elements.

17. A radiation imaging system comprising:

the radiation imaging apparatus according to claim 1; and a signal processor configured to process a signal from the radiation imaging apparatus.

18. The radiation imaging system according to claim 17, wherein the signal processor is configured to generate an energy subtraction image based on a signal output from each of a plurality of first conversion elements and a signal output from each of a plurality of second conversion elements.

19. A radiation imaging apparatus that comprises a first conversion element, a second conversion element, and a controller, wherein the first conversion element and the second conversion element have different sensitivities for detecting light, and the controller is configured to output, using a signal output from a measuring element configured to measure a dose of incident radiation, a stop signal configured to stop the radiation irradiation to the radiation imaging apparatus, and cause the first conversion element and the second conversion element to output signals configured to generate an energy subtraction image.

* * * * *